United States Patent [19]

Moukha et al.

[11] Patent Number: 5,972,672
[45] Date of Patent: Oct. 26, 1999

[54] *PHANEROCHAETE CHRYSOSPOIRIUM* STRAINS CNCM I-1511, I-1512 AND I-1513 FOR PRODUCING LIGNIN PEROXIDASE AND MANGANESE PEROXIDASE

[75] Inventors: Serge Moukha, La Ciotat; Jean-Claude Sigoillot, Six-Fours; Pierre Frasse, Marseilles; Marcel Asther, La Ciotat, all of France

[73] Assignee: Institut National de la Recherche Agronomique, Paris Cedex, France

[21] Appl. No.: 08/849,732

[22] PCT Filed: Dec. 28, 1995

[86] PCT No.: PCT/FR95/01746

§ 371 Date: Jul. 1, 1997

§ 102(e) Date: Jul. 1, 1997

[87] PCT Pub. No.: WO96/21008

PCT Pub. Date: Jul. 11, 1996

[30] Foreign Application Priority Data

Jan. 2, 1995 [FR] France .................................. 95 00002

[51] Int. Cl.⁶ .............................. C12N 9/08; C12N 1/14; C12N 11/00; C12N 11/08
[52] U.S. Cl. .......................... 435/192; 435/174; 435/176; 435/180; 435/254.1; 435/256.8; 435/911
[58] Field of Search ............................ 435/71.1, 41, 171, 435/183, 189, 192, 174, 180, 254.1, 256.8, 911

[56] References Cited

U.S. PATENT DOCUMENTS

| | | | |
|---|---|---|---|
| 5,153,121 | 10/1992 | Asther et al. | 435/71.1 |
| 5,342,765 | 8/1994 | Irvine et al. | 435/71.1 |

FOREIGN PATENT DOCUMENTS

| | | | |
|---|---|---|---|
| 2574427 | 6/1986 | France . | |
| 9004021 | 4/1990 | WIPO . | |

*Primary Examiner*—David M. Naff
*Attorney, Agent, or Firm*—Oblon, Spivak, McClelland, Maier & Neustadt, P.C.

[57] ABSTRACT

*Phanerochaete chrysosporium* strains CNCM numbers I-1511, I-1512 and I-1513 are found that produce increased amounts of manganese peroxidase (MnP) and lignin peroxidase (LiP). Immobilized cells may be used for culturing, and culture media is preferably supplemented with a phospholipid as a carbon source and/or veratryl alcohol to stabilize enzymes produced. Culturing conditions can be selected to modify the MnP/LiP ratio in favor of the production of MnP or LiP.

7 Claims, No Drawings

PHANEROCHAETE CHRYSOSPOIRIUM STRAINS CNCM I-1511, I-1512 AND I-1513 FOR PRODUCING LIGNIN PEROXIDASE AND MANGANESE PEROXIDASE

BACKGROUND OF THE INVENTION

1. Field of the Invention

The present invention relates to a process for producing peroxidases from the fungus *Phanerochaete chrysosporium*.

2. Description of the Background

*Phanerochaete chrysosporium* is a fungus associated with "white rot of wood". It is a hymenomycete which belongs to the order Aphylophorales and to the family Corticaceae. It has the property of degrading lignin to the point of mineralization (final products: $CO_2+H_2O$).

This fungus produces exocellular peroxidases: the latter comprise, in particular, isozymes of manganese peroxidase (MnPs) [KUWAHARA et al. FEBS Let., 169, pp. 247–250, (1984)] and those of lignin peroxidase (LiPs) [TIEN M. and KIRK T. K., Science, 221, pp. 661–663, (1983); GLENN et al. Biochem. Biophys. Res. Commun., 114, pp. 1077–1083]. These enzymes are glycosylated haemoproteins whose average molecular mass is 40 kDa [LEISOLA et al., J. Biol. Chem., 262 pp. 419–424, (1984)].

Manganese peroxidases and lignin peroxidases are capable of catalysing the oxidation of numerous aromatic substrates, especially lignin, using hydrogen peroxide as cosubstrate. These properties find their main applications in the field of papermaking and that of waste treatment.

Hitherto, the lignin peroxidases are the ones which have chiefly been used in this type of application.

For example, French Patent 2,574,427 describes two strains of *Phanerochaete chrysosporium* possessing especially high lignin peroxidase activity, and their culture on a medium containing an assimilable nitrogen source as well as an assimilable carbon source and a source of assimilable inorganic salts.

The proposal has also been made (French Patent 2,600,077) to culture *Phanerochaete chrysosporium* on a basal culture medium supplemented with unsaturated fatty acids and/or natural amino acids. Other teams have proposed adding detergent of the Tween type [FAISON and KIRK, Appl. Environ. Microbiol. (1985), 49, pp. 299–304], or alternatively adding veratryl alcohol [LEISOLA et al., J. Biotechnol. (1985), 3, pp. 97–107], in order to increase the synthesis of lignin peroxidase.

The inventors' team has also, in previous investigations, demonstrated various parameters whose optimization enabled the production of lignin peroxidase to be increased: addition of oleic acid and/or of exogenous phospholipids, control of the culture temperature, and the like. These investigations led to the development of a process for producing lignin peroxidase, which forms the subject of European Patent 0,437,500.

This process comprises several successive steps, each of them being performed under different culture conditions; the first step is performed on synthetic medium comprising inorganic salts, a carbon source and a nitrogen source, in the presence of yeast extract, a source of phospholipids and emulsified fatty acids; the mycelium formed is then cultured in a partially renewed culture medium, supplemented with veratryl alcohol but not comprising emulsified fatty acids, and whose phospholipid content represents only 1/7 to 1/8 of that of the culture medium used in the first step; in a third step, the medium is replaced completely by a new medium, comprising the same proportion of phospholipids and of veratryl alcohol as that of the second step, and the carbon source, the nitrogen source and the yeast extract at 1/4 of their content in the medium of the first step; lastly, a fourth culture step is performed in a medium lacking yeast extract, carbon source and emulsified fatty acids, but comprising the same proportion of phospholipids and of veratryl alcohol as that of the preceding steps.

The lignin peroxidase may then be recovered from the culture medium. The use of this process enables the enzyme content to be increased very significantly; the lignin peroxidase activity in the medium is approximately 240 U per liter and per day.

The research performed hitherto has mainly been concerned with increasing the lignin peroxidase activity. However, the manganese peroxidases are being seen increasingly to be capable of performing a key role in the bioconversion of polymeric aromatic compounds of the lignin type. In effect, contrary to lignin peroxidases whose activity is limited by the low penetration of the lignified walls by the enzyme, manganese peroxidases act via species of low molecular weight which diffuse readily. Briefly, the catalytic cycle of manganese peroxidases involves the oxidation of Mn(II) to Mn(III) which, after complexing with organic acids, generates diffusing oxidizing species capable of depolymerizing natural lignin [WARIISHI K., et al., Biochem. Biophys. Res. Comm. 176, pp. 269–276, (1991)].

BONNARME and JEFFRIES [J. Ferment. Bioeng. 70:158–163 (1990)] studied the regulation of the production of *Phanerochaete chrysosporium* lignin peroxidase and manganese peroxidase under different culture conditions; they observed in this way that the amount of these enzymes varied especially in accordance with the Mn(II) concentration: at low concentration, lignin peroxidase is produced preferentially (760 nmol/ml.min under optimal conditions), while at high concentration, the production of manganese peroxidase (950 nmol/ml.min under optimal conditions) is the one which is favoured.

SUMMARY OF THE INVENTION

It was the objective of the inventors to increase the production of *Phanerochaete chrysosporium* exocellular peroxidases from cultures of this fungus, and also to increase the MnP/LiP ratio.

For this purpose, the inventors succeeded in obtaining new strains (hereinafter designated MIC 390, MIC 249 and MIC 396) which are hypersecretory of the exocellular peroxidases lignin peroxidase and manganese peroxidase. In addition, they devised specific culture conditions which can be carried out either with free cells or with cells immobilized on a support. This enables the yield of lignin peroxidase and manganese peroxidase to be increased very significantly relative to that obtained with the cultures of the prior art: for example, the cultures obtained according to the invention can produce approximately twice as much lignin peroxidase as those of Patent EP 0,437,500, and 10 times as much manganese peroxidase as those obtained previously by BONNARME and JEFFRIES.

Implementation of the present invention makes it possible, in addition, to control and modify the manganese peroxidase/lignin peroxidase ratio according to requirements.

DETAILED DESCRIPTION OF THE INVENTION

The subject of the present invention is *Phanerochaete chrysosporium* strains MIC 249, MIC 390 and MIC 396, which were deposited on 20th December 1994 with the CNCM (Collection Nationale de Cultures de Microorganismes [National Collection of Microorganism Cultures]) held by the Pasteur Institute, 26 rue du Docteur Roux in Paris, under the respective numbers I-1511, I-1512 and I-1513.

The subject of the present invention is also a process for producing lignin peroxidase and/or manganese peroxidase from a culture of *Phanerochaete chrysosporium*, which process is characterized in that it comprises the culturing of at least one *Phanerochaete chrysosporium* strain chosen from the group consisting of the strains MIC 249, MIC 390 and MIC 396 mentioned above.

These cultures are produced, according to the standard techniques of culture of *Phanerochaete chrysosporium* which are known per se, from an inoculum consisting of mycelial fragments obtained from a preculture or from spores ($2 \times 10^5$ spores per ml approximately).

The culture medium comprises at least one carbon source, at least one nitrogen source, inorganic salts, trace elements and vitamins, and it is supplemented with yeast extract.

The concentration of the carbon source is preferably between 5 and 20 g/l.

A carbon source preferentially used comprises glycerol, but other carbon sources which are assimilable more slowly or more rapidly can be used, alone or mixed; examples of such carbon sources include maltose, raffinose, starch, xylose, rhamnose, arabinose, fructose, sorbitol, mannose, cellobiose and cellulose.

According to a preferred embodiment of the process according to the invention, the carbon source comprises at least one phospholipid chosen from the group consisting of phosphatidylcholine (PC), lysophosphatidylcholine (LPC), phosphatidylethanolamine (PE), acylphosphatidylethanolamine (APE), phosphatidylinositol (PI) and phosphatidic acid (PA), or a mixture of the said phospholipids; the mixture can, in this case, be a reconstituted mixture of phospholipids, or alternatively a mixture of phospholipids originating from a natural source, for example soya phospholipids. Advantageously, if a mixture of phospholipids is used, it comprises more than 25% of phosphatidylinositol and less than 15% of PC.

Preferably, the concentration of the phospholipid or mixture of phospholipids (reconstituted, or originating from soya) is between 0.1 and 10 g/liter.

The nitrogen source can, for example, consist of amino acids, sodium nitrate or a mixture of these different nitrogen sources, in combination with yeast extract. The concentration of the nitrogen source is preferably between 0.5 and 20 g/l.

The assimilable inorganic salts comprise potassium, calcium and magnesium salts, and are used at a concentration of between 0.5 and 100 mM.

The trace elements are mainly composed of iron sulphate, zinc sulphate, manganese sulphate and copper sulphate. The concentrations of iron, zinc and copper sulphates are the concentrations customarily used for culturing *Phanerochaete chrysosporium* (see, for example, European Patent 0,437, 500). The $Mn^{2+}$ concentration has no influence on the production of manganese peroxidase under the culture conditions according to the invention, and can vary over a relatively wide range; it is preferably between 1 and 600 mM.

The medium is also supplemented with a source of vitamins; it is possible, for example, to use a mixture of vitamins whose composition conforms to that given by TATUM et al. [Am. J. Bot., 37:38–46 (1950)]. The mixture of vitamins is used at a concentration of between 0.001 g and 1 g per liter.

Moreover, the addition of veratryl alcohol (approximately 0.4 mM) enables the stability of the enzymes produced to be maintained.

According to a preferred embodiment of the present invention, the culture medium is, in addition, supplemented during culture by adding, in the proportion of 0.001 to 10 grammes per liter, at least one component which activates the production of enzymes and/or protects the latter; this activating and/or protective component can consist of one of the constituents of the initial medium, or of a mixture of several of them.

Preferably, this activating and/or protective component comprises veratryl alcohol, which is, in this case, used at a concentration of between 0.1 and 1 gramme per liter. It is also possible to add a supplement of a phospholipid source rich in phosphatidylinositol, which is, in this case, used in the proportion of 0.1 to 3 grammes per liter.

This addition may be performed, in the form of a solution, emulsion or liposomes, by adding a mixture of surfactant (Tween 80 for example) with fatty acids (C18:12, C18:2) and phospholipids rich in phosphatidylinositol.

The supplementation of the medium may be performed continuously (pump) or discontinuously.

The supplementation with activating and/or protective component(s) is performed when the culture has reached a growth stage such that the expression of the genes coding for the peroxidases (production of the messenger RNAs coding for the manganese peroxidases and lignin peroxidases) is beginning to take place. This stage, which has been defined experimentally, is reached after a period which can vary according to the strains and the culture conditions, but which generally represents approximately 2 days of culture at a temperature of between 28° C. and 40° C.

To carry out the process according to the invention, culturing may be performed in a manner known per se, either with cells immobilized on a support or with free cells.

In the case of immobilized cells, the latter are coupled to or adsorbed on one or several hydrophobic, hydrophilic or neutral supports, the surface of which is preferably rough, and containing, for example, cavities, meshing (gauze or web), hollows or holes. These supports, hollow or otherwise, are arranged in ordered fashion or otherwise, fixed or mobile in the liquid phase consisting of the appropriate nutrient medium, and can have a variety of shapes (cylindrical or cubic, in one or several pieces). These supports, like the medium, may be replaced and/or renewed continuously or discontinuously during culture.

As non-limiting examples of unordered fixed supports, there may be mentioned cylindrical Raschig rings made of stoneware, glass, metal or plastic; polyurethane, polyester and polyamide foams; metal or plastic filings and plastic thread.

As non-limiting examples of ordered fixed supports, there may be mentioned gauze or meshing: stainless steel, glass, plastic, polyurethane, polyester, nylon, polyacrylate, polyamide, and the like.

As non-limiting examples of supports which are mobile in the liquid phase, there may be mentioned polyurethane, polyester, polyamide and extruded plastic supports.

In the case of free cells, the mycelium is in the form of balls which can be 0.5 to 5 mm in diameter. The bioreactors employed are of the bubble column or airlift type (diameter/ height ratio d/h=¼ to ⅙ approx.) or conventional type (d/h=1 to ½ approx.), and possess a specific or non-specific stirrer module, for example: Rushton, marine-type propeller, MIG, or single or double helical band.

Advantageously, culturing is performed with aeration and agitation of the medium.

Aeration of the medium is carried out by introducing air, pure oxygen or any other mixture of gases providing a sufficient supply of oxygen to the microorganism, by means of a device permitting homogeneous dispersion of this gas (sintered glass, rod).

Agitation of the medium may be performed mechanically. It can also be obtained pneumatically by direct action of the aeration system, or by an equivalent system used simultaneously.

The level of agitation and/or of aeration is chosen so as to permit a homogeneous initial occupation of the support in the case of immobilized cells, and the formation of mycelial balls of average diameter 0.5 to 5 mm in the case of free cells, while limiting the shearing stresses undergone by the mycelial hyphae. This level may be variable during the culture period.

Advantageously, in the initial period (approximately 2 days), incubation takes place at a temperature of approximately 37° C, and can be followed by a temperature change favourable to the production of peroxidases, as described, for example, in Patent EP 0,437,500.

The production of manganese peroxidase and/or that of lignin peroxidase, and consequently the MnP/LiP ratio, can be controlled in accordance with the age of the culture and/or the presence of activators, as well as the strains used. It is thus possible to obtain enzyme cocktails which predominate either in manganese peroxidase or in lignin peroxidase (activity greater than or equal to 60% of the collective manganese peroxidase and lignin peroxidase activities).

According to a variant of the process according to the invention, it is possible, in addition, to control the MnP/LiP ratio, and to increase preferentially either the production of manganese peroxidase or the production of lignin peroxidase. This variant is characterized in that:

to modify the MnP/LiP ratio in favour of the production of manganese peroxidase, culturing of *Phanerochaete chrysosporium* is carried out for a period of more than 24 hours and less than 90 hours in the presence of a mixture of phospholipids rich in phosphatidylinositol, as is defined above, at a concentration of between 0.5 and 5 g/l, preferably of the order of 1.5 g/l;

to modify the MnP/LiP ratio in favour of the production of lignin peroxidase, culturing of *Phanerochaete chrysosporium* is carried out for a period of more than 90 hours and less than 350 hours in the presence of a mixture of phospholipids, as is defined above, at a concentration of between 0.5 and 5 g/l.

Depending on the applications, the culture liquors thus constituting enzyme cocktails more or less enriched in manganese peroxidase or in lignin peroxidase may be used directly, or after concentration, for example by ultrafiltration. Where appropriate, purification on a MONO-Q type column (Pharmacia Biotech S.A.; France) is carried out.

A better understanding of the present invention will be gained from the further description which follows, which refers to examples of embodiment of the process according to the invention.

It should be clearly understood, however, that these examples are given only by way of illustration of the subject of the invention, of which they in no way constitute a limitation.

I—Use of Hypersecretory Strains

The strains which were selected according to the invention are the *Phanerochaete chrysosporium* strains MIC 249 (CNCM I-1511), MIC 390 (CNCM I-1512) and MIC 396 (CNCM I-1513).

EXAMPLE 1

Comparison of the Production of Lignin Peroxidases and of Manganese Peroxidases by Different Strains The production capacity of the hypersecretory strains according to the invention, MIC 249, MIC 390 and MIC 396, relative to the reference strain BKM-F-1767 (ATCC 24725), is verified on cultures set up in 250-ml Erlenmeyers under the following conditions:

Composition of the medium

Glycerol 10 g/l

Disodium tartrate 2.3 g/l

Diammonium tartrate 1.842 g/l $KH_2PO_4$ 2 g/l $CaCl_2.2H_2O$ 0.14 g/l $MgSO_4.7H_2O$ 0.70 g/l $FeSO_4.7H_2O$ 0.07 g/l $ZnSO_4.7H_2O$ 0.046 g/l $MnSO_4.H_2O$ 0.035 g/l $CuSO_4.5H_2O$ 0.007 g/l Yeast extract 1 g/l Nat89 0.5 g/l Veratryl alcohol 0.42 g/l Culture conditions The medium is distributed under sterile conditions in the proportion of 100 ml per Erlenmeyer; each Erlenmeyer contains cubes of polyurethane foam.

Inoculation is carried out using mycelial fragments from a preculture.

Oxygenation of the Erlenmeyers is carried out at the start of culturing (T0), and incubation at 37° C is then carried out with stirring at 90 or 120 rpm.

From 48 h of culture, daily oxygenation of the Erlenmeyers is carried out, and incubation is continued at 37° C with stirring at 90 or 120 rpm.

The lignin peroxidase and manganese peroxidase activities are measured after 4 days of culture according to the following protocols:

a) determination of lignin peroxidase activity: this activity is determined by measuring the rate of oxidation of veratryl alcohol to the corresponding aldehyde in the presence of hydrogen peroxide [TIEN and KIRK, Proc. Natl. Acad. Sci. U.S.A. 81:2280–2284 (1984)]. The reaction is monitored at 30° C. by spectrophotometry at 310 nm. The molar extinction coefficient of veratraldehyde at this wavelength is 9300 $M^{-1}.cm^{-1}$.

The activity in the medium is expressed in $nkatal.ml^{-1}$ or alternatively in units/liter (U/l): one lignin peroxidase unit corresponds to one micromole of veratraldehyde formed per minute.

b) determination of manganese peroxidase activity: this activity is determined by measuring the rate of oxidation of vanillylacetone in the presence of $MnSO_4$ [PASZCZYNSKI et al. FEMS Microbiol. Lett., 29:37–41 (1985)]. The reaction is monitored at 30° C. by spectrophotometry at 334 nm. The molar extinction coefficient of vanillylacetone at this wavelength is 18300 $M^{-1}.cm^{-1}$.

The activity in the medium is expressed in $nkatal.ml^{-1}$ or alternatively in units/liter (U/l): one manganese peroxidase unit corresponds to one micromole of vanillylacetone formed per minute.

The results are summarized in Table I below:

TABLE I

| STRAIN | MnP ACTIVITY (U/l) | LiP ACTIVITY (U/l) |
|---|---|---|
| ATCC 24725 | 1200 | 900 |
| MIC 249 | 4800 | 4200 |
| MIC 390 | 5520 | 2040 |
| MIC 396 | 3500 | 3150 |

These results show that, under these conditions, the strain I-1511 (MIC 249) produces 4 times as much manganese peroxidase and lignin peroxidase as the reference strain BKM-F-1767; the strain I-1512 (MIC 390) produces approximately 5 times as much manganese peroxidase and twice as much lignin peroxidase as the strain BKM-F-1767; and the strain I-1513 (MIC 396) produces twice as much manganese peroxidase and lignin peroxidase as the strain BKM-F-1767.

II—Influence of the Composition of the Medium and the Culture Conditions on the Production of Lignin Peroxidases and of Manganese Peroxidases

EXAMPLE 2

Influence of the Age of the Culture

The strain MIC 249 is cultured under conditions identical to those described above in Example 1. Incubation is performed at 37° C. with stirring at 90 rpm.

The lignin peroxidase and manganese peroxidase activities are measured at various culture times, and the MnP/LiP ratio is calculated. The results are summarized in Table II below.

TABLE II

| AGE OF THE CULTURE (h) | MnP ACTIVITY (U/l) | LiP ACTIVITY (U/l) | MnP/LiP RATIO |
|---|---|---|---|
| 63 | 3270 | 1746 | 1.87 |
| 109.5 | 2694 | 2634 | 1.02 |
| 229 | 2346 | 4290 | 0.55 |

EXAMPLE 3

Influence of the Phospholipid Concentration

The strain MIC 390 is cultured under the following conditions, on a basal medium whose composition is as follows:

Glycerol 10 g/l
Disodium tartrate 2.3 g/l
Diammonium tartrate 1.842 g/l
$KH_2PO_4$ 2 g/l
$CaCl_2.2H_2O$ 0.14 g/l
$MgSO_4.7H_2O$ 0.70 g/l
$FeSO_4.7H_2O$ 0.07 g/l
$ZnSO_4.7H_2O$ 0.046 g/l
$MnSO_4.H_2O$ 0.035 g/l
$CuSO_4.5H_2O$ 0.007 g/l
Yeast extract 1 g/l This basal medium is supplemented with a mixture of phospholipids, NAT89, at concentrations of between 0.5 g/l and 1.89 g/l.

NAT 89 is supplied by the company NATTERMAN PHOSPHOLIPID GmbH (Cologne, Germany), and its composition is as follows:

12% of phosphatidylcholine and lysophosphatidylcholine;
31% of phosphatidylethanolamine and acylphosphatidylethanolamine;
27% of phosphatidylinositol;
30% of phophatidic acid.

Culturing is performed as described in Example 1. Incubation is performed at 37° C. with stirring at 120 rpm.

The lignin peroxidase and manganese peroxidase activities are measured at optimum production in the culture medium, namely at 4.5 days of culture.

The MnP/LiP ratio is calculated. The results are shown in Table III below.

TABLE III

| NAT89 CONCENTRATION (g/l) | MnP ACTIVITY (U/l) | LiP ACTIVITY (U/l) | MnP/LiP RATIO |
|---|---|---|---|
| 0.5 | 6564 | 1932 | 3.4 |
| 0.98 | 6780 | 1920 | 3.53 |
| 1.44 | 8664 | 1056 | 8.21 |
| 1.89 | 6474 | 384 | 16.86 |

III—Production of Lignin Peroxidases and Manganese Peroxidases in a Reactor

EXAMPLE 4

Culture in a Reactor Containing Cells Immobilized on a Support

The body of the bioreactor contains the immobilization support, which consists in this case of 2 concentric cylinders made of metal gauze (wire 0.15 mm in diameter) having a 0.5 mm mesh, respective diameters of 70 mm (outer cylinder) and 30 mm (inner cylinder) for a height of 290 mm.

The composition of the basal medium is as follows:
Glycerol 12.5 g/l
Disodium tartrate 2.875 g/l
Diammonium tartrate 2.302 g/l
$KH_2PO_4$ 2.5 g/l
$CaCl_2.2H_2O$ 0.175 g/l
$MgSO_4.7H_2O$ 0.875 g/l
$FeSO_4.7H_2O$ 0.0875 g/l
$ZnSO_4.7H_2O$ 0.0575 g/l
$MnSO_4.H_2O$ 0.0437 g/l
$CuSO_4.5H_2O$ 0.0087 g/l
Yeast extract 1.25 g/l
NAT89 0.625 g/l 2.5 liters of this medium are introduced into the bioreactor, and the whole is sterilized by autoclaving for 30 min at 120° C.

The bioreactor is then thermostated at 37° C. and is aerated with filtered atmospheric air, introduced at a flow rate of 40 l/h by means of a circular aeration rod or a sinter forming a steady stream of bubbles, located at the base of the metal cylinders, providing both for agitation and for a homogeneous aeration needed for the formation of a satisfactory mycelial film.

Inoculation is carried out using mycelial fragments from a preculture.

After 48 hours of culture:

A) The medium is supplemented under sterile conditions with a phospholipid mixture (NAT89) to which veratryl alcohol (VeA) is added.

Composition of the mixture:
VeA 1.25 g
NAT89 0.30 g

B) The stream of air bubbles is replaced by a stream of pure oxygen bubbles at a flow rate of 20 l/h.

The manganese peroxidase and lignin peroxidase activities obtained under these conditions with the strain MIC 390 are:

maximum MnP activity: 10000 U/l
maximum LiP activity: 2400 U/l.

EXAMPLE 5

Culture of the Microorganism in a Reactor Containing Free Cells, of the Bubble Column Type The composition of the basal medium is as follows:
Glycerol 6.8 g/l
Disodium tartrate 1.565 g/l
Diammonium tartrate 1.252 g/l
$KH_2PO_4$ 1.334 g/l
$CaCl_2.2H_2O$ 0.094 g/l
$MgSO_4.7H_2O$ 0.467 g/l
$FeSO_4.7H_2O$ 0.0461 g/l
$ZnSO_4.7H_2O$ 0.0310 g/l
$MnSO_4.H_2O$ 0.0232 g/l
$CuSO_4.5H_2O$ 0.0046 g/l
Yeast extract 0.680 g/l
NAT89 0.5 g/l 2.5 liters of this medium are introduced into the bioreactor, and the whole is sterilized by autoclaving for 30 min at 120° C.

The bioreactor is then thermostated at 37° C. and aerated with filtered atmospheric air, introduced at a flow rate of 40 l/h by means of a circular aeration rod or a sinter forming a steady stream of bubbles, providing both for agitation and for a homogeneous aeration needed for the formation of mycelial balls.

Inoculation is carried out using mycelial fragments from a preculture or a solution of spores containing $2 \times 10^5$ spores/ml.

After 24 h, the mycelial balls 0.5 to 1 mm approximately in diameter are formed, and the air flow rate is reduced to 20 l/h.

After 48 h:

A) The medium is supplemented under sterile conditions with a phospholipid mixture comprising veratryl alcohol (VeA).

Composition of the mixture:
VeA 1.05 g
phospholipid source 0.25 g

B) The stream of air bubbles is replaced by a stream of pure oxygen bubbles at a flow rate of 20 l/h.

The results obtained under these conditions with the strain MIC 390 are:
maximum MnP activity: 3600 U/l
maximum LiP activity: 162 U/l.

We claim:

1. A biologically pure *Phanerochaete chrysospoirium* strain having CNCM number I-1511, I-1512 or I-1513.

2. A process for producing lignin peroxidase and/or manganese peroxidase from a culture of *Phanerochaete chrysosporium*, comprising culturing at least one *Phanerochaete chrysosporium* strain selected from the group consisting of CNCM number I-1511 1-1512 and I-1513.

3. The process according to claim 2, wherein the culture medium of *Phanerochaete chrysosporium* is supplemented during culture by adding veratryl alcohol at a concentration of between 0.1 and 1 g/l, and/or a phospholipid source rich in phosphatidylinositol in the proportion of 0.1 to 3 g/l.

4. The process according to claim 3, wherein the supplementation with phospholipids and/or with veratryl alcohol is performed after approximately 2 days of culture at a temperature of between 28° C. and 40° C.

5. The process according to claim 2, including the preferential increase either of the production of manganese peroxidase (MnP) or of the production of lignin peroxidase (LiP), as follows:

to modify the MnP/LiP ratio in favour of the production of manganese peroxidase, the culturing of *Phanerochaete chrysosporium* is carried out for a period of more than 24 hours and less than 90 hours in the presence of a mixture of phospholipids at a concentration of between 0.5 and 5 g/l;

to modify the MnP/LiP ratio in favour of the production of lignin peroxidase, the culturing of *Phanerochaete chrysosporium* is carried out for a period of more than 90 hours and less than 350 hours in the presence of a mixture of phospholipids whose concentration is between 0.5 and 5 g/l.

6. The process according to claim 2, wherein a culture of cells immobilized on a support is used.

7. The process according to claim 2, wherein a culture of free cells is used.

* * * * *